US008653236B2

(12) United States Patent
Agrez et al.

(10) Patent No.: US 8,653,236 B2
(45) Date of Patent: Feb. 18, 2014

(54) THERAPEUTIC AGENTS

(75) Inventors: Michael Valentine Agrez, Charlestown (AU); Douglas Dorahy, Garden Suburb (AU)

(73) Assignee: Inter-K Pty Limited (AU)

( * ) Notice: Subject to any disclaimer, the term of this patent is extended or adjusted under 35 U.S.C. 154(b) by 0 days.

(21) Appl. No.: 13/384,435

(22) PCT Filed: Jul. 17, 2009

(86) PCT No.: PCT/AU2009/000915
§ 371 (c)(1),
(2), (4) Date: May 9, 2012

(87) PCT Pub. No.: WO2010/006377
PCT Pub. Date: Jan. 21, 2010

(65) Prior Publication Data
US 2012/0244123 A1 Sep. 27, 2012

(30) Foreign Application Priority Data

Jul. 17, 2008 (AU) .............................. 2008903653

(51) Int. Cl.
*A61K 38/04* (2006.01)
*A61K 38/10* (2006.01)
*C07K 7/00* (2006.01)
*C07K 7/08* (2006.01)

(52) U.S. Cl.
USPC ............... 530/324; 530/326; 530/327; 514/2; 514/12; 514/14

(58) Field of Classification Search
USPC ........ 530/300, 324, 325, 326, 327; 514/2, 12, 514/13, 14
See application file for complete search history.

(56) References Cited

U.S. PATENT DOCUMENTS

| 5,807,746 | A | 9/1998 | Lin et al. |
|---|---|---|---|
| 5,830,667 | A | 11/1998 | Alvarez |
| 5,877,282 | A | 3/1999 | Nadler et al. |
| 6,043,339 | A | 3/2000 | Lin et al. |
| 6,248,558 | B1 | 6/2001 | Lin et al. |
| 6,312,956 | B1 | 11/2001 | Lane |
| 6,432,680 | B1 | 8/2002 | Lin et al. |
| 6,495,518 | B1 | 12/2002 | Hawiger et al. |
| 6,780,843 | B2 | 8/2004 | Lin et al. |
| 7,183,105 | B2 | 2/2007 | Sabbadini |
| 7,396,822 | B2 | 7/2008 | Sabbadini et al. |
| 7,611,885 | B2 | 11/2009 | Brahmbhatt et al. |
| 8,003,091 | B2 | 8/2011 | Brahmbhatt et al. |
| 2004/0147435 | A1 | 7/2004 | Hawiger et al. |

FOREIGN PATENT DOCUMENTS

| WO | 9534295 | A1 | 12/1995 |
|---|---|---|---|
| WO | 9628563 | A1 | 9/1996 |
| WO | 9816241 | A1 | 4/1998 |
| WO | 9949879 | A1 | 10/1999 |
| WO | 0137821 | A1 | 11/2000 |

OTHER PUBLICATIONS

Kim et al, Brain Res. Bull. 47(1):35-41, 1998.*
Poussu et al, N.A.R 33(12):e104, pp. 1-8, 2005.*
Eddleman, Indiana Biolab; http://www.disknet.com/indiana_biolab/b122.htm, 1998.*
Polard, P. et al., "Bacterial transposases and retroviral integrases", Molecular Microbiology, 1995, 15(1), p. 13-23.
GenBank Accession No. ZP_00379476. Apr. 8, 2005.
GenBank Accession No. ZP_00380870. Apr. 8, 2005.
Adessi, C. and Soto, C., Converting a Peptide into a Drug: Strategies to Improve Stability and Bioavailability. Current Medicinal Chemistry, 2002, 9, pp. 963-978.
Cardozo, A.K., et al., Cell-permeable peptides induce dose- and length-dependent cytotoxic effects. Biochimica et Biochimica et Biophysica Acta, 2007, 1768, pp. 2222-2234.
Cloninger, M. J., Biological applications of dendrimers, Current Opinion in Chemical Biology, 2002, vol. 6, pp. 742-748.
De Boer, P. A., et al., A Division Inhibitor and a Topological Specificity Factor Coded for by the Minicell Locus Determine Proper Placement of the Division Septum in *E.coli*, Cell, Feb. 24, 1989, vol. 56, pp. 641-649.
Derossi, D., et al., Cell Internalization of the Third Helix of the Antennapedia Homeodomain Is Receptor-independent, Journal of Biological Chemistry, Jul. 26, 1996, vol. 271, No. 30, pp. 18188-18193.
Derossi, D., et al., The Third Helix of the Antennapedia Homeodomain Translocates through Biological Membranes, The Journal of Biological Chemistry, Apr. 8, 1994, vol. 269, No. 14, pp. 10444-10450.
Dixon, J. S., Evaluation of the CASP2 Docking Section, Proteins: Structure, Function and Genetics, Suppl., 1997, 1, pp. 198-204.
Duncan, R. and Izzo, L., Dendrimer biocompatibility and toxicity, Advanced Drug Delivery Reviews, 2005, 57, pp. 2215-2237.
Jin, Y., et al., Antimicrobial Activities and Structures of Two Linear Cationic Peptide Families with Various Amphipathic β-Sheet and α-Helical Potentials, Antimicrobial Agents and Chemotherapy, Dec. 2005, vol. 49, No. 12, pp. 4957-4964.
Jones, D. T., Critically assessing the state-of-the-art in protein structure prediction, The Pharmacogenomics Journal, 2001, 1, pp. 126-134.
Lee, C. C., et al., Designing dendrimers for biological applications, Nature Biotechnology, Dec. 2005, vol. 23, No. 12, pp. 1517-1526.
Lensink, M. F., et al., Docking and scoring protein complexes: CAPRI 3rd Edition, Proteins, 2007, 69, pp. 704-718.
Macdiarmid, J. A., et al., Bacterially Derived 400 nm Particles for Encapsulation and Cancer Cell Targeting of Chemotherapeutics, Cancer Cell, 2007, 11, pp. 431-445.

(Continued)

*Primary Examiner* — Kevin Hill
(74) *Attorney, Agent, or Firm* — Morriss O'Bryant Compagni

(57) ABSTRACT

A purified anti-cancer peptide consisting of amino acids 266 to 287 of Genbank Accession No. O68604 (SEQ ID No. 4), and modified and homologous forms of the peptide are described. The modified or and homologous forms of the peptide include more than contiguous amino acids having at least 75% amino acid sequence identity with at least 8 contiguous amino acids of amino acids 266-287 of Genbank Accession No. O68604 (SEQ ID No. 4) defining a motif selected from the group consisting of RRRVQQ (SEQ ID No. 5) and RGRAK (SEQ ID No. 1). The peptide(s) can be produced by *B. linens*, a *Brevibacterium* commonly used in the production of cheese. There is also provided method for prophylaxis or treatment of cancer in a mammal, comprising treating the mammal with an effective amount of the peptide, or a protein the pepsin cleavage of which yields the peptide.

16 Claims, 5 Drawing Sheets

(56) References Cited

OTHER PUBLICATIONS

Onraedt, A., et al., Industrial importance of the genus *Brevibacterium*, Biotechnology Letters, 2005, 27, pp. 527-533.

Pooga, M., et al., Cell penetration by transportan, The FASEB Journal, Jan. 1998, vol. 12, pp. 67-77.

Prochiantz, A., Getting hydrophilic compounds into cells: lessons from homeopeptides, Current Opinion in Neurobiology, 1996, 6, pp. 629-634.

Rice, P. A. and Baker, T. A., Comparative architecture of transposase and integrase complexes, Nature Structural Biology, Apr. 2001, vol. 8, No. 4, pp. 302-307.

Sadler, K. and Tam, J. P., Peptide dendrimers: applications and synthesis, Reviews in Molecular Biotechnology, 2002, 90, pp. 195-229.

Skolnick, J. and Fetrow, J. S., From genes to protein structure and function: novel applications of computational approaches in the genomic era, TIBTech, Jan. 2000, vol. 18, pp. 34-39.

Tame, J. R.H., Scoring functions: A view from the bench, Journal of Computer-Aided Molecular Design, 1999, 13, pp. 99-108.

Tosatto, S.C.E. and Toppo, S., Large-Scale Prediction of Protein Structure and Function from Sequence, Current Pharmaceutical Design, 2006, 12, pp. 2067-2086.

Trommsdorff M., et al., Interaction of Cytosolic Adaptor Proteins with Neuronal Apolipoprotein E Receptors and the Amyloid Precursor Protein, Journal of Biological Chemistry, Dec. 11, 1998, vol. 273, No. 50, pp. 33556-33560.

\* cited by examiner

```
(i)     D D V R R R V Q Q E T T G H R G R A K D P L Y R
(ii)    D V C R R R V Q Q A T C G H R G R A G D P L Y K
(iii)   D E C R R R V Q L A T C G H R G R S T D P L Y R
(iv)    D E C R R R V Q H D I L G R R G R K N D P L Y K
(v)     D E A R R R V Q Q A P S G N R G R T S D P L Y G
(vi)    T V C R Q R I Q Q A T T G H R G R G G D P L Y G
(vii)   D X X R R R V Q Q X T X G H R G R X K D P L
```

22C :   DDVRRRVQQETTGHRGRAKDPL – COOH

14C :   H- DDVRRRVQQETTGH-COOH

8C :                           RGRAKDPL – COOH

THERAPEUTIC AGENTS

FIELD OF THE INVENTION

The invention relates to peptides having antiproliferative activity against cancer cells. The invention also relates to compositions and methods for the prophylaxis or treatment of cancer.

BACKGROUND OF THE INVENTION

Cationic antimicrobial peptides are found in most living organisms as components of their non-specific defenses against pathogens. They have been identified in bacteria, fungi, plants, insects, amphibians, crustaceans, fish, birds and mammals including man, and can be expressed constitutively or induced in response to the presence of a microbe. Although the mode of action of cationic peptides is not well understood, these peptides are thought to interact with cell membranes as part of their action against microbes. The linear cationic sequence RGRAK (SEQ ID. No. 1) is a feature of a class of cationic antimicrobial peptides that form an amphipathic beta-sheet conformation that may be selective in targeting bacterial cells over mammalian cells.

The NPXY consensus motif (SEQ ID No. 2) is a sorting signal present within the cytosolic domain of proteins and is important for the sorting of transmembrane proteins to different compartments of the endosomal-lysosomal system. The NPXY motif is a tyrosine-based sorting signal and is recognized by components of protein coats peripherally associated with the cytosolic surface of membranes. Postulated recognition proteins for NPXY signals are clathrin, AP-2 and Dab2.

Amongst a growing number of cell-penetrating peptides that are able to penetrate cell membranes and translocate different cargoes into cells is the prototypical sequence constituting the viral peptide known as TAT (48-60) (GRKKRRQRRRPPQ) (SEQ ID. No. 3), derived from the HIV-1 Tat protein. Whilst the entire Tat protein is 86 amino acids in length and contains a highly basic region required for translocation activity, the Tat (48-60) peptide is a minimally active sequence containing a 9 amino acid stretch of basic residues required for membrane lytic activity. Tat 48-60 has been shown to be useful in translocating DNA across cell membranes, producing an increase in transfection efficiency over control peptides.

*Brevibacterium linens* has long been recognized as an important dairy microorganism because its application to the surface of a variety of cheeses, such as Limburger, Münster, Brick, Tilster, Appenzeller and Camembert, provides flavour, colour and suppresses growth of other bacteria (e.g., see Onraedt et al, 2005). *B. linens* is an aerobic microorganism with a rod-coccus growth cycle, having a temperature growth optimum of 20° C. to 30° C. It is a halotolerant organism with optimum growth at pH 6.5 to 8.5. The growth of *B. linens* is thought to be an essential prerequisite for the aroma of smear surface-ripened cheeses.

Transposases are ubiquitous non-secreted, intracellular enzymes that catalyse genetic rearrangement within and between genomes through a series of metal-dependent phosphoryl transfer reactions. Putative DNA transposases may be identified via sequence similarity and/or specific signatures in the encoded transposases.

SUMMARY OF THE INVENTION

The present invention stems from the surprising finding that a peptide fragment encoded by a putative DNA transposase (GenBank Accession No. O68604) of *Brevibacterium linens* exhibits antiproliferative activity against cancer cells. The peptide contains partial amino acid sequences that resemble functionally defined motifs. Moreover, as the peptide is resistant to pepsin digestion, peptide integrity and the spatial relationship between these amino sequences may be maintained upon oral ingestion of the peptide. Whilst the mechanism of the anti-cancer activity of the peptide is unknown, this unexpected finding lends itself to the use of the peptide and peptide agents based on this peptide in the prophylaxis or treatment of cancer. In addition, the established use of *B. linens* in the production of soft cheeses suggests that such agents exhibit low or no toxicity in humans, particularly in normal cells of the gastrointestinal epithelium.

In one aspect of the invention there is provided a purified anti-cancer peptide consisting of amino acids 266 to 287 of Genbank Accession No. O68604 (namely DDVR-RRVQQETTGHRGRAKDPL (SEQ ID No. 4), or a modified or homologous form of the peptide, the modified or homologous form of the peptide including at least one complete or partial form of a motif selected from the group consisting of RRRVQQ (SEQ ID No. 5) and RGRAK (SEQ ID No. 1), and more than 5 contiguous amino acids having at least 75% amino acid sequence identity with at least 8 contiguous amino acids of amino acids 266-287 of Genbank Accession No. O68604 (SEQ ID No. 4) that define the motif.

In another aspect of the invention there is provided a method for prophylaxis or treatment of cancer in a mammal, comprising treating the mammal with an effective amount of an anti-cancer peptide consisting of amino acids 266 to 287 of Genbank Accession No. O68604 (SEQ ID No. 4) or a modified or homologous form of the peptide, the modified or homologous form of the peptide including at least one complete or partial form of a motif selected from the group consisting of RRRVQQ (SEQ ID No. 5) and RGRAK (SEQ ID No. 1), and more than 5 contiguous amino acids having at least 75% amino acid sequence identity with at least 8 contiguous amino acids of amino acids 266-287 of Genbank Accession No. O68604 (SEQ ID No. 4) that define the motif.

In another aspect of the invention there is provided a method for inhibiting growth of a cancer cell, comprising contacting the cell with an effective amount of an anti-cancer peptide consisting of amino acids 266 to 287 of Genbank Accession No. O68604 (SEQ ID No. 4) or a modified or homologous form of the peptide, the modified or homologous form of the peptide including at least one complete or partial form of a motif selected from the group consisting of RRRVQQ (SEQ ID No. 5) and RGRAK (SEQ ID No. 1), and more than 5 contiguous amino acids having at least 75% amino acid sequence identity with at least 8 contiguous amino acids of amino acids 266-287 of Genbank Accession No. O68604 (SEQ ID No. 4) that define the motif.

In another aspect of the invention there is provided a pharmaceutical composition, comprising an anti-cancer peptide consisting of amino acids 266 to 287 of Genbank Accession No. O68604 (SEQ ID No. 4) or a modified or homologous form of the peptide, the modified or homologous form of the peptide including at least one complete or partial form of a motif selected from the group consisting of RRRVQQ (SEQ ID No. 5) and RGRAK (SEQ ID No. 1), and more than 5 contiguous amino acids having at least 75% amino acid sequence identity with at least 8 contiguous amino acids of amino acids 266-287 of Genbank Accession No. O68604 (SEQ ID No. 4) that define the motif, together with a pharmaceutically acceptable carrier and/or excipient.

As peptides embodied by one or more forms of the invention can be produced by *Brevibacterium* commonly used in the production of cheese, the regular intake of cheese containing this bacteria may provide prophylaxis or treatment of cancer. Accordingly, there is also provided a method for prophylaxis or treatment of cancer in a mammal, comprising treating the mammal with an effective amount of a cheese comprising *B. linens* or other *Brevibacterium* which produces a protein the pepsin cleavage of which yields a peptide embodied by the invention, the treatment comprising the consumption of the cheese.

In a further aspect of the invention there is provided a nutritive supplement for consumption by a mammal, comprising a purified anti-cancer peptide consisting of amino acids 266 to 287 of Genbank Accession No. O68604 (SEQ ID No. 4) or a modified or homologous form of the peptide, the modified or homologous form of the peptide including at least one complete or partial form of a motif selected from the group consisting of RRRVQQ (SEQ ID No. 5) and RGRAK (SEQ ID No. 1), and more than 5 contiguous amino acids having at least 75% amino acid sequence identity with at least 8 contiguous amino acids of amino acids 266-287 of Genbank Accession No. O68604 (SEQ ID No. 4) that define the motif, together with an edible carrier and/or excipient.

In a further aspect there is provided a method for prophylaxis or treatment of cancer in a mammal, comprising treating the mammal with an effective amount of a bacterial organism that expresses a peptide embodied by the invention or a protein which when cleaved by pepsin releases a peptide of the invention, or an extract of the bacterial organism, the extract containing the peptide or protein, and the treatment comprising consumption of the bacterial extract or the extract.

The bacterial organism can be engineered to express the protein or peptide, and can be a *Brevibacterium*.

In another aspect there is provided the use of a peptide embodied by the invention in the prophylaxis or treatment of cancer in a mammal.

In one or more embodiments, the pharmaceutical composition or nutritive supplement described herein includes a cellular preparation or extract thereof of an organism that expresses a protein or an anti-cancer peptide according to the invention.

Moreover, in at least some forms, a modified or homologous form of the peptide embodied by the invention can include a complete, partial or homologous form of a DPL motif (SEQ ID No. 6).

Typically, a modified or homologous form of a peptide embodied by the invention has at least 75% amino acid sequence identity with at least 8 contiguous amino acids of amino acids 266-287 of Genbank Accession No. O68604 (SEQ ID No. 4) that define a motif selected from the group consisting of RRRVQQ (SEQ ID No. 5) and RGRAK (SEQ ID No. 1).

In at least some modified forms of a peptides embodied by the invention, respective of the motifs of the peptide are located in relative positions to the corresponding motif(s) of SEQ ID No. 4. Most usually, the motifs (or partial sequence(s) thereof) of the modified peptides will be in homologous positions to the corresponding motif(s) of SEQ ID. No. 4. The modified or homologous form of the peptide can for instance comprise the peptide consisting of amino acids 266-289 of GenBank Accession No. O68604 (SEQ ID No. 7), also referred to herein as peptide 24-NH2.

Respective of the motif(s) of a modified or homologous form of peptide will normally comprise at least a majority of the amino acids of the corresponding motif of the peptide consisting of amino acids 266 to 287 of GenBank Accession No. O68604 (SEQ ID No. 4).

A peptide embodied by the invention can have respective complete or partial forms of both the RRRVQQ (SEQ ID No. 5) and RGRAK (SEQ ID No. 1) motifs.

Typically, a peptide embodied by the invention having respective complete or partial forms of both the RRRVQQ (SEQ ID No. 5) and RGRAK (SEQ ID No. 1) motifs will not have a pepsin cleavage site between the motifs.

In at least some forms, a homologous form of the peptide can be a peptide fragment of a DNA transposase.

It will also be understood that a peptide embodied by the invention can be a naturally occurring, recombinant, or artificially synthesized or derived peptide, prepared by any suitable conventionally known means.

In further aspects, there is provided a nucleic acid sequence encoding a peptide embodied by the invention, and a recombinant vector incorporating the nucleic acid. Generally, the recombinant vector will be an expression vector for expression of the peptide in the host cell.

In another aspect there is provided a host cell transformed with a recombinant vector incorporating a nucleic acid sequence that encodes an anti-cancer peptide according to the invention.

In another aspect there is provided a host cell transformed with a nucleic acid sequence that encodes an anti-cancer peptide according to the invention, wherein the nucleic acid sequence is integrated into the genome of the host cell.

In addition, the invention extends to the use of a peptide embodied by the invention in the manufacture of a medicament for prophylaxis or treatment of a cancer.

As used in the context of the present invention, the term "cancer" encompasses any type of unregulated cell proliferation. The cancer may be a cancer of any tissue origin.

Further, the term "purified" in the context of peptides by the invention encompasses peptides that have been at least partially purified, and preparations including the peptide mixed with one or more other components. For example, a nutritive supplement or composition embodied by the invention are examples of such preparations.

The mammal can be any mammal treatable with a method of the invention, and can be a member of the bovine, porcine, ovine or equine families, a laboratory test animal such as a mouse, rabbit, guinea pig, a cat or dog, a primate or human being.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The features and advantages of the invention will become further apparent from the following description of non-limiting embodiments together with the accompanying drawings.

BRIEF DESCRIPTION OF THE ACCOMPANYING DRAWINGS

referred to herein as "22C" is derived (shown in bold) upon theoretical digestion with pepsin forms Pn2 (active at pH>2) and Pn1.3 (active at pH 1.3).

Figures 4, 5A:
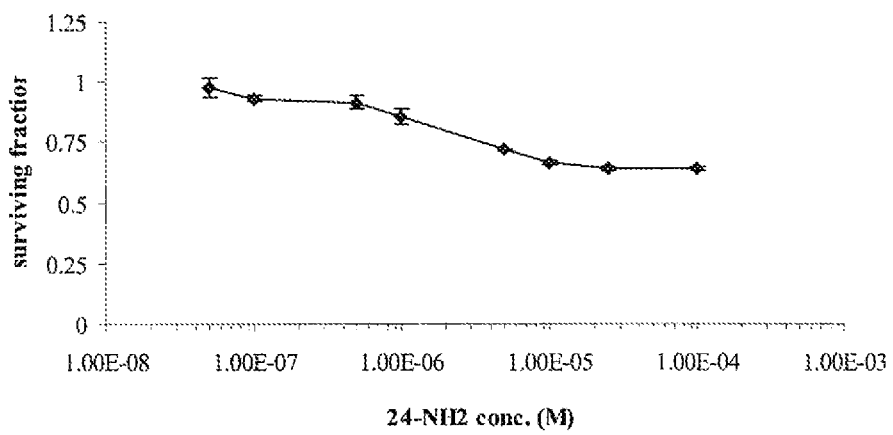

FIG. 4 shows a BLAST-P analysis of *B. linens* peptide 24-NH2 identifying six 24-NH2-like sequences (SEQ ID No. 9-14) each of which are resident in putative transposase proteins. Conserved amino acids are shown in bold and peptide fragments produced following theoretical pepsin digestion are shown underlined (Expasy Peptide Cutter program). (i) 24-NH2; (ii) *Arthrobacter* sp. TM1. (Acc. AAC28267); (iii) Orf2 *Mycobacterium smegmatis* (Acc. AAA98489); (iv) Plasmid pEST1226 (Acc. AAC64902); (v) *Propionibacterium acnes* KPA171202 (Acc. YP_055571); (vi) *Rhodococcus erythropolis* PR4 (Acc. YP_345706); (vii) Consensus sequence (SEQ ID No 15) for a peptide embodied by the present invention, wherein X denotes an amino acid that does not result in the generation of a pepsin cleavage site between the complete or partial RRRVQQ (SEQ ID No. 5), RGRAK (SEQ ID No. 1) and DPL (SEQ ID No. 6) motifs.

FIG. 5 (A) is a graph showing the effect of *B. linens* peptide 24-NH2 (SEQ ID. No. 7) on the growth of HT29 colorectal adenocarcinoma cells in a serum-containing MTT cell proliferation assay. (B) shows the amino acid sequences of two peptides 14C (SEQ ID No. 16) and 8C (SEQ ID No. 17) derived from the *B. linens* peptide 22C (SEQ ID. No. 4). (C) is a graph showing the effect of *B. linens* peptides 22C, 14C and 8C on the growth of HT29 colorectal adenocarcinoma cells in a serum-free MTT cell proliferation assay. (D) is a graph showing the effect of *B. linens* peptides 22C, 14C and 8C on the growth of HT29 colorectal adenocarcinoma cells in a serum-containing MTT cell proliferation assay.

Figure 6:
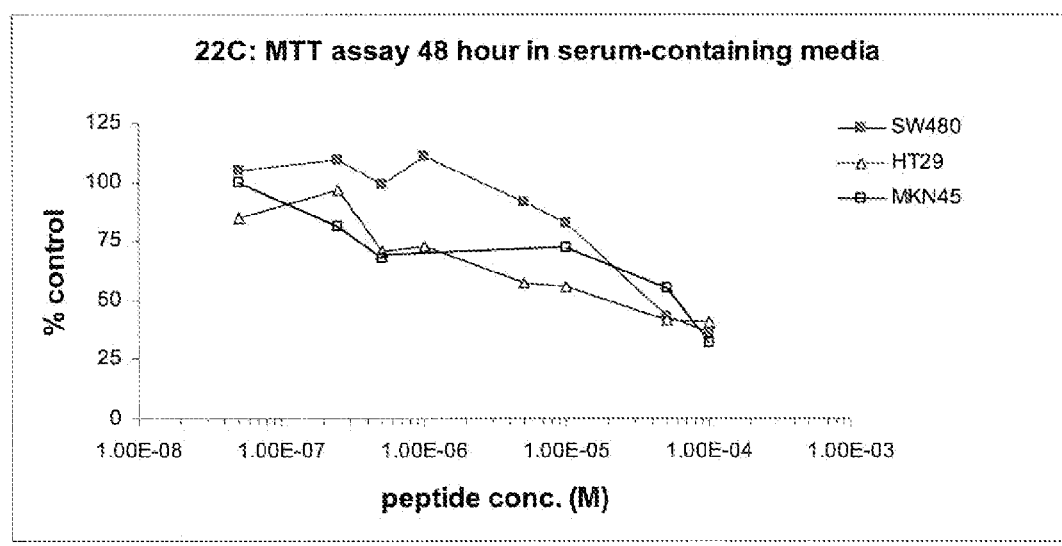

FIG. 6 is a graph showing the effect of *B. linens* peptide 22C (SEQ ID No. 4) on the growth of HT20 colorectal adenocarcinoma cells, SW480 colon carcinoma cells and MKN45 gastric carcinoma cells in a serum-containing MTT cell proliferation assay.

DETAILED DESCRIPTION OF EXEMPLARY EMBODIMENTS OF THE INVENTION

The inventors have identified a peptide sequence contained in a putative DNA transposase of *B. linens* (GenBank Accession No. O68604, National Centre for Biotechnology Information, U.S. National Library of Medicine, 8600 Rockville Pike, Bethesda, Md., United States) possessing the ability to inhibit the growth of cancer cells. The peptide contains several peptide motifs resembling functionally defined linear peptide sequences, and although the mechanism of antiproliferative activity of the peptide is unknown, studies performed by the inventors suggest the motifs or at least partial sequences thereof are relevant to the antiproliferative activity of the peptide. The derivation of a peptide from *B. linens* having anticancer properties indicates that the consumption of smear surface-ripened cheeses fermenting this organism or other *Brevibacterium* which can produce proteins the pepsin cleavage of which produces a peptide embodied by the invention may have considerable health benefits in the prevention of cancer, particularly cancers of gastrointestinal origin.

Modified and homologous forms of the peptide defined by amino acids 266-287 of GenBank Accession No. O68604 (SEQ ID No. 4) include active fragments of the peptide, and retain anti-proliferative activity against cancer cells. For example, an active fragment of SEQ ID No. 4 is one that retains at least some anti-cancer activity of the peptide defined by SEQ ID No. 4.

The amino acid sequence of a modified or homologous form of a peptide embodied by the invention can have one or more amino acid changes compared to SEQ ID No. 4 or an active peptide fragment thereof. The anti-cancer activity of the peptide will also typically be essentially retained or provided by the modified or homologous peptide.

A modified peptide embodied by the invention can for example be provided by the addition, deletion and/or substitution of one or more amino acids compared to SEQ ID No. 4. Inversion of amino acids and other mutational changes that result in alteration of an amino acid sequence are also encompassed. A modified peptide can be prepared by introducing nucleotide changes in a nucleic acid sequence coding for the amino acid sequence of SEQ ID No. 4, such that the desired amino acid changes are achieved upon expression of the mutagenised nucleic acid or for instance, by synthesising an amino acid sequence incorporating the desired amino acid changes.

The substitution of an amino acid can involve a conservative or non-conservative amino acid substitution. By conservative amino acid substitution is meant replacing an amino acid residue with another amino acid having similar charge and stereochemical properties which does not substantially affect the anticancer activity of the peptide. Preferred modified peptides include ones having amino acid sequences in which one or more amino acids have been substituted with alanine or other neutrally charged amino acid residue(s), or to which one or more such amino acid residues have been added. A modified peptide can also incorporate an amino acid or amino acids not encoded by the genetic code, or amino acid analog(s). For example, D-amino acids rather than L-amino acids can be utilised. Indeed, a peptide as described herein may consist partly or entirely of D amino acids. D-peptides may be produced by chemical synthesis using techniques that are well-known in the art. Hence, some embodiments of peptides may include L-amino acids, D-amino acids or a mixture of L- and D-amino acids. The synthesis of peptides including D-amino acids can inhibit peptidase activity (e.g., endopeptidase) as is known in the art, and thereby enhance stability and increase the half-life of the peptide in vivo compared to the corresponding L-peptide.

Further, a peptide as described herein can for example be N- and/or C-protected to render them less resistant to degradation by proteases in vivo or to inhibit their clearance from the circulation via the kidneys. Methods such as pegylation of peptides are well known in the art and all such methods are expressly encompassed. Typically, a pegylated peptide/protein used in a method embodied by the invention will be coupled to 2 or more monomers of polyethylene glycol (PEG) (e.g., (PEG)n) where n is typically in a range of from about 2 to about 11.

The homology between a modified or homologous peptide as described herein with SEQ ID No. 4 (or active fragment of SEQ ID No. 4) is determined by comparing amino acids at each position in the sequences when optimally aligned for the purpose of comparison. The sequences are considered homologous at a position if the amino acids at that position are the same. Alignment of sequences can be performed using any suitable program or algorithm such as for instance, by the Needleman and Wunsch algorithm (Needleman and Wunsch, 1970). Computer assisted sequence alignment can be conveniently performed using standard software programs such as GAP which is part of the Wisconsin Package Version 10.1 (Genetics Computer Group, Madison, Wis., United States) using the default scoring matrix with a gap creation penalty of 50 and a gap extension penalty of 3.

An active fragment, modified or homologous peptide embodied by the invention can have a sequence length of more than 5 amino acids up to about 35 amino acids or more.

In one or more forms, the modified or homologous peptide can be about 20 to 30 amino acids in length, for example having 20, 21, 22, 23, 24, 25, 26, 26, 27, 28, 29 or 30 amino acids. Typically, an active fragment, modified or homologous peptide will be more than 5 and usually, up to about from to 22 amino acids in length, for example having 7, 8, 9, 10, 11, 12, 13, 14, 15, 16, 17, 18, or 19 amino acids etc. Nevertheless, it will be understood peptides that are 31, 32, 33, and 34 amino acids in length are also expressly encompassed as are peptides within ranges falling with the length ranges indicated above. For example, an active fragment, modified or homologous peptide having a length in a range of from 8 to 35 amino acids, 14 to 25 amino acids or for instance, 17 to 26 amino acids or the like are all specifically encompassed by the invention.

Typically, a peptide comprising a complete or partial RGRAK motif (SEQ ID No. 1) will be at least 8 amino acids in length. A peptide comprising a complete or partial RRRVQQ motif (SEQ ID No. 5) will typically be at least 14 amino acids in length.

A further modified peptide embodied by the invention comprises the amino acid sequence $DX_1X_2RRRVQQX_3TX_4GHRGRX_5KDPL$ (SEQ ID No. 15) wherein $X_n$ denotes an amino acid or amino acid analog (e.g., a synthetic amino acid not encompassed by the genetic code or molecule which acts as a substitute for the native/wild-type amino acid) that does not result in the generation of a pepsin cleavage site between the complete or partial RRRVQQ (SEQ ID No. 5), RGRAK (SEQ ID No. 1) and DPL (SEQ ID No. 6) motifs. The amino acids at any one of the five X positions can for example be independently selected from any one of the twenty known amino acids or from known amino acid analogs, wherein the selected amino acids essentially do not diminish antiproliferative activity of the native peptide. In some embodiments, the amino acid or amino acid analog at $X_1$ can be negatively charged, the amino acid or amino acid analog at $X_2$ can be polar, the amino acid or amino acid analog at $X_3$ can be hydrophobic, and the amino acids or amino acid analogs at $X_4$ and $X_5$ can be polar.

A modified peptide as described herein may also comprise or consist of the amino acid sequence DRRRVQQTGHRGRKDPL (SEQ ID No. 18).

In some embodiments, a modified peptide may comprise the amino acid sequence of SEQ ID No. 7 (peptide 24-NH2).

Further, active fragments encompassed by the present invention include the 14 mer peptide DDVRRRVQQETTGH (SEQ ID No. 16) and the 8 mer peptide RGRAKDPL (SEQ ID No. 17). An active fragment, or modified and/or homologous peptide may also be provided comprising both of these sequences with or without a pepsin cleavage site provided between them. A modified and/or homologous peptide may also for example, include one of SEQ ID No. 16 or SEQ No. 17 and a modified or homologous form of the other of SEQ ID No. 16 or SEQ ID No. 17, again with or without a pepsin cleavage site between those sequences.

Partial forms of the motif defined by RGRAK (SEQ ID No. 1) include RSRAK (SEQ ID No. 19), RGRSK (SEQ ID No. 20) and RSRSK (SEQ ID No. 21). The motif DPL (SEQ ID No. 6) resembles the functional motif NPXY (SEQ ID No. 2), and partial forms of SEQ ID No. 6 include NPL (SEQ ID No. 22). Hence, modified and homologous forms of peptides as described herein include those with one or more of these partial motifs. Typically, a peptide including a partial or complete form of the RGRAK motif (SEQ ID No. 1) will include the DPL motif (SEQ No. 6) (or a partial form thereof as described herein) C-terminal to the complete or partial RGRAK motif (SEQ ID No. 1).

Typically, the motif(s) of a modified or homologous peptide embodied by the invention will respectively have at least about 80% sequence identity with the corresponding motif of SEQ ID. No. 4 and more usually about 85%, 90%, or 95% sequence identity with the corresponding motif of SEQ ID No. 4 or more. A modified or homologous peptide will also generally have an overall amino acid sequence identity with SEQ ID. No. 4, SEQ ID. No. 16 or SEQ ID. No. 17, of at least about 50%, 60%, 65%, 70%, 75% or greater and most preferably, about 80%, 90%, 95% or 98% or greater. It will also be understood that all possible specific sequence identity percentages within the ranges specified above also are expressly encompassed by the invention.

A peptide embodied by the invention may be constrained in a three dimensional conformation for antiproliferative activity. For example, it may be synthesised with side chain structures or with cysteine residues which form a disulfide bridge, or otherwise be incorporated into a molecule with a known stable structure in vivo. For example, the peptide may be incorporated into an amino acid sequence at least part of which folds into a β-pleated sheet or helical structure such as an α-helix.

A peptide can also be cyclised to provide enhanced rigidity and thereby stability in vivo. Various methods for cyclising peptides and fusion proteins are known. For example, a synthetic peptide incorporating two cysteine residues distanced from each other along the peptide may be cyclised by the oxidation of the thiol groups of the residues to form a disulfide bridge between them. Cyclisation may also be achieved by the formation of a peptide bond between the N-terminal and C-terminal amino acids of a synthetic peptide or for instance through the formation of a bond between the positively charged amino group on the side chain of a lysine residue and the negatively charged carboxyl group on the side chain of a glutamine acid residue. As will be understood, the position of the various amino acid residues between which such bonds are formed will determine the size of the cycle. Variation of cycle size for optimisation of binding affinity can be obtained by synthesising peptides in which the position of amino acids for achieving cyclisation has been altered. The formation of direct chemical bonds between amino acids or the use of any suitable linker to achieve a desired three-dimensional conformation is also well within the scope of the skilled addressee.

Typically, the N-terminal and/or C-terminal ends of peptides embodied by the present invention having antiproliferative activity will be modified to protect against or inhibit in vivo degradation by endopeptidases. For instance, the C-terminus of the peptides may be amidated to protect against endopeptidase degradation and peptides with a C-terminal amido group are preferred for use in methods of the invention.

Strategies for identifying peptides suitable for use in methods of the present invention include large scale screening techniques. For example, peptide library protocols and in particular phage peptide display libraries provide an efficient way of testing a vast number of potential agents. Such libraries and their use are well known. Prospective agents identified may be then further evaluated in suitable activity, competitive and other assay. A method of screening for a peptide or evaluating whether a peptide is capable of inhibiting cancer cell growth will typically involve utilising the peptide in an assay employing conditions whereby cancer cells are treated with the peptide, and determining whether inhibition of cell growth occurs, as compared to control peptides.

As an alternative to the administration of a peptide of the invention to a mammal, a nucleic acid molecule encoding a peptide or fusion protein may be administered to the mammal, for expression of the peptide or fusion protein within the cancer cells to effect inhibition of growth of a cancer cell. The nucleic acid sequence can be introduced into the cells in an appropriate expression vector for expression of the nucleic acid sequence extra-chromosomally or for integration of the nucleic acid sequence into genomic DNA by recombination events prior to expression of the peptide or fusion protein. Alternatively, the cells can be transfected with a nucleic acid molecule incorporating nucleotide sequences flanking the sequence encoding the peptide or fusion protein which facilitate recombination with genomic DNA for expression of the encoded agent under the control of the transfected cell's own transcriptional regulatory sequences.

A particularly preferred way of achieving intracellular delivery of peptides, nucleic acids and other agents is to use a "facilitator moiety" such as a carrier peptide, which has the ability to deliver cargo macro-molecules across cell membranes in an energy-independent manner. Such carrier peptides provide the possibility of both testing potential agents in cell culture without drastically altering cell membrane integrity and of delivering agents in vivo. Carrier peptides that are known in the art include penetratin and variants thereof (e.g., Derossi D et al, 1994, 1996), human immunodeficiency virus Tat derived peptide (e.g., Prochiantz A, 1996), transportan derived peptide (e.g., Pooga M et al, 1998), and signal peptides including modified forms and partial sequences thereof, and all such molecules can be utilized in a method embodied by the invention.

Rather than a carrier peptide, the facilitator moiety can be a lipid moiety or other non-peptide moiety which enhances cell membranes solubility of the agent, such that passage of the agent across the cell membrane is facilitated. The lipid moiety may for instance be selected from triglycerides including mixed triglycerides. Fatty acids are preferred and particularly, $C_{16}$-$C_{20}$ fatty acids. Typically, the fatty acid will be a saturated fatty acid and most preferably, a stearic acid. The invention is not limited to the use of any such non-peptide facilitator moiety, and any molecule which provides the desired cell membrane solubility that is physiologically acceptable may be used.

In the instance the agent is a nucleic acid encoding a peptide of the invention, the facilitator moiety will typically also be capable of passage through the nuclear membrane of eukaryotic cells and thereby effecting translocation of the attached nucleic acid into the nucleus.

A peptide embodied by the present invention can be linked to the facilitator moiety in any conventionally known manner. For instance, a peptide may be linked directly to a carrier peptide through an amino acid linker sequence by a peptide bond or non-peptide covalent bond using a cross-linking reagent. For agents that have a negative charge such as nucleic acids, the agent may be linked to the carrier peptide by charge-association between the negatively charged agent and the positively charged amino acids in the carrier peptide or linker sequence. Chemical ligation methods may also be used to create a covalent bond between the carboxy terminal amino acid of the carrier peptide or linker sequence and the peptide embodied by the invention.

Various further methods can also be employed to enhance the half-life of a peptide embodied by the invention or for facilitating passage of the peptides into target cancer cells. Such methods include incorporating the peptide(s) into dendrimers.

Provision of the peptides in dendrimer form is particularly suitable for facilitating delivery of the peptides to target cells. Dendrimers comprise a relatively large branched framework/scaffolding to which multiple copies of the peptide are coupled. The dendrimer can be any dendrimer deemed suitable for use in methods embodied by the invention. For instance, the dendrimer can have branched organic framework to which the peptides are coupled, such as framework formed by poly (amidoamine) (PAMAM), tris(ethylene amine) ammonia or poly (propylene imine) (Astramol™). In other forms, the dendrimer can have a framework incorporating polyamino acids forming branching units to which the peptide is coupled. The amino acids can be encoded by the genetic code and/or other amino acids. In at least some embodiments, the dendrimer has a framework of branching units formed by lysine amino acid residues, and the peptides of the invention are coupled to the lysine residues.

Peptide dendrimers are particularly suitable for use in methods of the invention and in at least some embodiments of the invention, comprise polypeptides coupled to a branched framework of polyamino acids (typically lysine branching units). The dendrimer will typically have at least 3 layers/generations of amino acid branching units, the polypeptides being coupled to the outermost layer/generation of the amino acid branching units such that the dendrimer presents a plurality of units of the polypeptide as further described below. While momoner units of the polypeptide are preferred, in other embodiments, dendrimers incorporating multiple units of the polypeptide (e.g., DDVRRRVQQETTGH)n, (i.e., (SEQ ID No. 16)n), wherein n is the number of units of the polypeptide (typically 1-3)) coupled to polyamino acid branching units of the dendrimer may be utilised.

The polypeptide can be grafted onto the surface of the outermost layer/generation of polyamino acid branching units forming the framework of the dendrimer, or be synthetically assembled on the polyamino acid branching units of the dendrimer. More particularly, the synthesis of dendrimers useful in one or more methods embodied by the invention can be achieved by divergent or convergent synthesis strategies.

The divergent strategy is a direct approach by which the dendrimer is built stepwise in a continuous operation on a solid support through solid-phase synthesis. Stepwise synthesis involves synthesis of the branching core of the dendrimer followed by synthesis of the polypeptide inhibitor in a continuous manner. The divergent strategy is particularly suitable for the synthesis of dendrimers with a framework of a trifunctional acid (e.g., polyamino acid). Such solid phase synthesis schemes are the method of choice for the synthesis of lysine branching units where di-protected lysine is used to produce a branching framework of multiple levels of lysines. The diamino nature of lysine results in each additional level of lysine effectively doubling the number of sites upon which the polypeptide inhibitor may be synthesized directly.

The convergent strategy is an indirect, modular approach by which the polypeptide and branching core unit are prepared separately and then coupled together. Core units with branching framework used in the convergent synthesis of dendrimers are commercially available, and are typically formed from organic amino compounds such as poly (amidoamine) (PAMAM), tris(ethylene amine) ammonia or poly (propylene imine) (Astramol™) to which separately prepared inhibitor is normally covalently linked.

Figure 1:
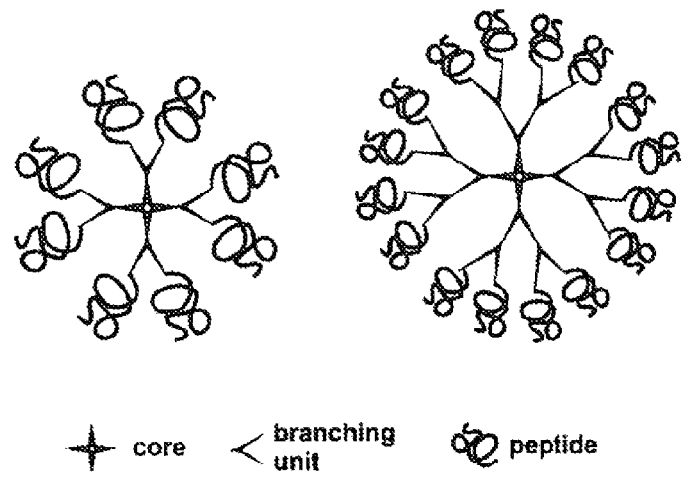
FIG. 1 is a schematic illustration of peptide dendrimer of a type that may be used in one or more embodiments of methods as described herein.
Figure 2:
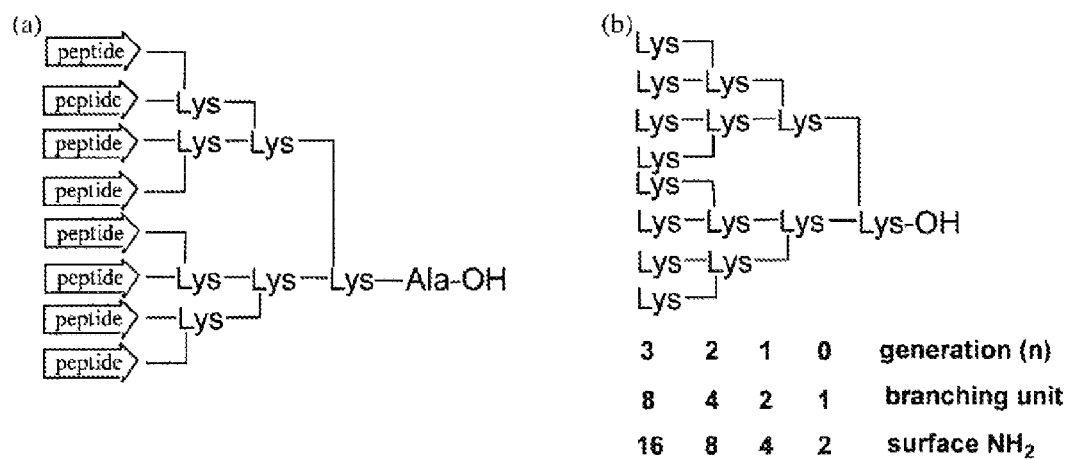
FIG. 2 (A) is a schematic illustration of a multiple antigen peptide dendrimer (MAP), incorporating eight peptide monomers. (B) An increase in the number of Lys branching units increases the number of surface amine groups.

Suitable peptide dendrimer framework to which peptides as described herein can be coupled, and methods for the provision of peptide dendrimers, are for example described in Lee et al, 2005; Sadler and Tam, 2002; and Cloninger, 2002, the entire contents of which are incorporated herein in their entirety by reference. Examples of peptide dendrimers suitable for use in embodiments of the present invention are schematically illustrated in FIG. 1 and FIG. 2 (Sadler, K., and Tam, J. P., *Rev. in Mol. Biotechnology*, Vol. 90, Issues 3-4, May 2002, pgs 195-229).

Typically, the dendrimer will present 4, 6, 8 or more peptide units embodied by the invention, generally at least 8 of the peptide monomer units and more usually, at least 10 of the peptide units. Further, the peptides presented by the dendrimer may be pegylated as described above.

Another approach for the direct targeting of peptides embodied by the invention to cancer cells involves the use of nano-sized particles, also known as minicells, that encapsulate high concentrations of the peptide and are targeted to tumour cell-surface receptors through bispecific antibodies coating the minicells (e.g., see MacDiamid, J. A. 2007 the entire contents of which is expressly incorporated herein by cross-reference). In particular, bacterial minicells can be utilized. These are anucleate nanoparticles produced as a result of inactivating the genes that control normal bacterial cell division (De Boer P. A., 1989). Receptor engagement results in minicell endocytosis, intracellular degradation, and release of active peptide within the cancer cell, and the use of all such minicells to encapsulate and deliver the peptides of the invention to the target cancer cells is expressly encompassed by the invention. Such minicells may be formulated for injection, or for oral consumption whereupon the peptide is subsequently released from the minicell for uptake via the small intestine. It will also be understood that minicells may be used to deliver dendrimers as described herein to the target cancer cells.

Peptides embodied by the present invention can be directly synthesized by established synthetic processes. Alternatively, the peptides can be sourced from naturally occurring species of *Brevibacterium* through large scale fermentation of the bacteria, the methodology for which is known in the art and described in for example in U.S. Pat. No. 5,470,732. Thus, a peptide embodied by the present invention can be purified directly from a naturally occurring bacterium.

Alternatively, the peptide can be obtained from a recombinant source, for example, a *Brevibacterium* or other host bacterium transfected with an expression vector containing the nucleic acid sequence encoding the peptide. Other forms of the peptide that can be obtained through recombinant DNA techniques include a recombinant fusion protein incorporating the peptide. Thus, the provision of fusion proteins and use of fusion proteins incorporating a peptide embodied by the present invention is expressly provided for by the invention. Peptides and fusion proteins or the like as described herein can be synthesised or produced using conventional peptide synthesis or recombinant techniques. Nucleic acid encoding a fusion protein can for instance be provided by joining separate DNA fragments encoding peptides or polypeptides having desired three dimensional conformations and/or amino acid sequences by employing blunt-ended termini and oligonucleotide linkers, digestion to provide staggered termini as appropriate, and ligation of cohesive ends. Alternatively, PCR amplification of DNA fragments can be utilised employing primers which give rise to amplicons with complementary termini which can be subsequently ligated together (e.g., see Ausubel et al. (1994) Current Protocols in Molecular Biology, USA, Vol. 1 and 2, John Wiley & Sons, 1992; Sambrook et al (1998) Molecular cloning: A Laboratory Manual, Second Ed., Cold Spring Harbour Laboratory Press, New York).

Peptides and fusion proteins may be expressed in vitro and purified from cell culture for administration to the mammalian subject, or cells may be transfected with nucleic acid encoding the peptide or fusion protein for in vitro or in vivo expression thereof. The nucleic acid will typically first be introduced into a cloning vector and amplified in host cells, prior to the nucleic acid being excised and incorporated into a suitable expression vector for transfection of cells.

Typical cloning vectors incorporate an origin of replication (ori) for permitting efficient replication of the vector, a reporter or marker gene for enabling selection of host cells transformed with the vector, and restriction enzyme cleavage sites for facilitating the insertion and subsequent excision of the nucleic acid sequence of interest. Preferably, the cloning vector has a polylinker sequence incorporating an array of restriction sites. The marker gene may be drug-resistance gene (e.g., $Amp^r$ for ampicillin resistance), a gene encoding an enzyme such as chloramphenicol acetyltransferase (CAT), β-lactamase, adenosine deaminase (ADA), aminoglycoside phosphotransferase (APH), dihydrofolate reductase (DHFR), hygromycin-B-phosphotransferase (HPH), thymidine kinase (TK), or for instance β-galactosidase encoded by the *E. coli* lacZ gene (LacZ'). Yeast reporter genes include imidazole glycerolphosphate dehydratase (HIS3), N-(5'-phosphoribosyl)-anthranilate isomerase (TRP1) and β-isopropylmalate dehydrogenase (LEU2). As will be appreciated, expression vectors of the invention may also incorporate such marker genes.

Cloning vectors include cloning vectors for mammalian, yeast and insect cells. Particular vectors that may find application include pBR322 based vectors and pUC vectors such as pUC118 and pUC119. Suitable expression and cloning vectors are also for instance described in Sambrook et al (1998) Molecular Cloning. A Laboratory Manual., Sambrook et al., 2nd Ed. Cold Spring Harbour Laboratory, 1989.

Suitable expression vectors include plasmids and cosmids capable of expression of a DNA (e.g., genomic DNA or cDNA) insert. An expression vector will typically include transcriptional regulatory control sequences to which the inserted nucleic acid sequence is operably linked. By "operably linked" is meant the nucleic acid insert is linked to the transcriptional regulatory control sequences for permitting transcription of the inserted sequence without a shift in the reading frame of the insert. Such transcriptional regulatory control sequences include promoters for facilitating binding of RNA polymerase to initiate transcription, expression control elements for enabling binding of ribosomes to transcribed mRNA, and enhancers for modulating promoter activity. A promoter may be a tissue specific promoter which facilitates transcription of the nucleic acid insert only in specific cell lineages and not in other cell types or only to a relatively low level in such other cell types. The design of an expression vector will depend on the host cell to be transfected, the mode of transfection and the desired level of transcription of the nucleic acid insert.

Numerous expression vectors suitable for transfection of prokaryotic (e.g., bacterial) or eukaryotic (e.g., yeast, insect or mammalian cells) are known in the art. Expression vectors suitable for transfection of eukaryotic cells include pSV2neo, pEF.PGK.puro, pTk2, pRc/CNV, pcDNAI/neo, non-replicating adenoviral shuttle vectors incorporating the polyadenylation site and elongation factor 1-a promoter and pAdEasy based expression vectors most preferably incorporating a cytomegalovirus (CMV) promoter. For expression in insect cells, baculovirus expression vectors may be utilised examples of which include pVL based vectors such as pVL1392, and pVL941, and pAcUW based vectors such as pAcUW1.

Any means for achieving the introduction of the nucleic acid into a target cell can be used. Transfer methods known in the art include viral and non-viral transfer methods. Suitable virus into which appropriate viral expression vectors may be packaged for delivery to target cells include adenovirus, vaccinia virus, retroviruses of avian, murine and human origin, herpes viruses including Herpes Simplex Virus (HSV) and EBV, papovaviruses such as SV40, and adeno-associated virus. Particularly preferred virus are replication deficient recombinant adenovirus. Engineered virus may be administered locally or systemically to achieve delivery of nucleic acid sequence into a target cell.

Rather than utilising viral mediated transfection of cells, nucleic acid sequences and other agents may be introduced into a cell in vitro or in vivo by liposome mediated transfection. The liposomes may carry targeting molecules for maximising delivery of the nucleic acids contained therein to specific cell types of interest. Such targeting molecules include antibodies or binding fragments thereof as described above, ligands or cell surface receptors for facilitating fusion of liposomes to the specific cells of interest. Nucleic acids may also be intracellularly delivered in vitro using conventional cold or heat shock techniques or for instance, calcium phosphate coprecipitation or electroporation protocols as are known in the art. Yet another strategy is to design the agent to have the inherent ability to pass across the lipid bilayer of a cell.

While expression of the proteins or peptides of the invention may be obtained by transforming suitable host cells with expression vectors as described above, the nucleic acid encoding the protein or peptide of the invention may alternatively be integrated directly into the genome of the host cell, typically along with a suitable promoter sequence to drive expression of the protein or peptide within the host cell. Following insertion of the nucleic acid into host cells, the cells may be screened to identify cultures or cell lines that exhibit stable, reproducible expression of the nucleic acid and concomitant production of the desired protein, fusion protein or peptide. Stable integration and expression of nucleic acids within a variety of host cells are well known in the art, and include for example the use of yeast (EP19880870152) and bacterial expression systems.

Host cells that can be used for expression of polypeptides or fusion proteins include bacteria and probiotic bacteria such as *E. coli, B. subtilis, Lactococcus lactis, Streptomyces* and *Pseudomonas, Brevibacterium* and particularly *B. linens* bacterial strains, yeast such as *Sacchromyces* and *Pichia*, insect cells, avian cells and mammalian cells such as Chinese Hamster Ovary cells (CHO), COS, HeLa, HaRas, W138, SW480, and NIH3T3 cells. The host cells are cultured in a suitable culture medium under conditions for facilitating expression of the introduced nucleic acid prior to purification of the expressed product from the host cells, and/or supernatants as the case may be using standard purification techniques.

The toxicity profile of a peptide can be tested on normal and cancer cells by evaluation of cell morphology, trypan-blue exclusion, assessment of apoptosis and cell proliferation studies (e.g., cell counts, $^3$H-thymidine uptake and MTT assay).

A peptide having antiproliferative activity against cancer cells as described herein can also be co-administered with one or more other compounds or drugs. For example, an agent or agents may be co-administered in combination or in conjunction with antisense therapy or one or more chemotherapeutic drugs. In particular, in the instance a drug resistant cancer is being treated, the agent(s) can be co-administered to the mammal in combination or in conjunction with the chemotherapeutic drug to which cells of the cancer are resistant. By "co-administered" is meant simultaneous administration in the same formulation or in two different formulations by the same or different routes, or sequential administration by the same or different routes such that the peptides and drugs/agents exert their effect in overlapping therapeutic windows.

By "sequential" administration is meant one is administered after the other typically although not necessarily, with a time delay of from very short times from minute(s) up to several hours.

The peptide or peptides will typically be formulated into a pharmaceutical composition incorporating a pharmaceutically acceptable carriers and/or excipient for administration to the intended subject. Pharmaceutical compositions include sterile aqueous solutions suitable for injection, (where the agent or agents is water soluble) and sterile powders for the extemporaneous preparation of sterile injectable solutions. The carrier may be a solvent or dispersion medium containing one or more of physiological saline, ethanol, polyol (e.g., glycerol, propylene glycol, liquid polyethylene glycol and the like), vegetable oils and mixtures thereof. Fluidity may be maintained by the use of a coating such as lecithin and by the use of surfactants.

Injectable solutions will typically be prepared by incorporating the peptide in the desired amount in the selected solvent with various other components enumerated above, prior to sterilizing the solution by filtration. Generally, dispersions will be prepared by incorporating the peptide into a vehicle which contains the dispersion medium and other components.

For oral administration, the peptide(s) may be formulated into any orally acceptable carrier deemed suitable. In particular, the peptide may be formulated with an inert diluent, an assimilable edible carrier or it may be enclosed in a hard or soft shell gelatin capsule. Moreover, a peptide as described herein may be incorporated with excipients and used in the form of ingestible tablets, bucal tablets, troches, capsules, elixirs, suspensions or syrups. Enteric formulations for facilitating passage to the stomach for uptake/delayed uptake via the small intestines are also well known to the skilled addressee and are expressly encompassed by the present invention.

Peptides embodied by the invention can also be formulated into topically acceptable carriers conventionally used for forming creams, lotions or ointments for internal or external application. Topical formulations may be applied to a site to be treated by dressings and the like impregnated with the formulation.

Typically, a composition of the invention will incorporate one or more preservatives such as parabens, chlorobutanol, phenol, sorbic acid, and thimerosal. In many cases, a composition may furthermore include isotonic agents such as sugars or sodium chloride. Prolonged absorption/uptake of the peptide may be brought about by the use in the compositions of agents for delaying absorption such as aluminium monostearate and gelatin.

Tablets, troches, suppositories, pills, capsules may also contain one or more of a binder such as gum tragacanth, acacia, corn starch or gelatin; a disintegrating agent such as corn starch, potato starch or alginic acid; and a lubricant such as magnesium stearate. Where the agent is to be administered orally, the composition may also comprise a sweetening agent such as sucrose, lactose or saccharin; and a flavouring agent.

Pharmaceutically acceptable carriers include any suitable conventionally known solvents, dispersion media and isotonic preparations or solutions. Use of such ingredients and media for pharmaceutically active substances is well known. Except insofar as any conventional media or agent is incompatible with the active agent, use thereof in therapeutic and prophylactic compositions is included. Supplementary active ingredients can also be incorporated into the compositions if desired.

It is particularly preferred to formulate oral compositions in dosage unit form for ease of administration and uniformity of dosage. Dosage unit form as used herein is to be taken to mean physically discrete units suited as unitary dosages for the mammalian subject to be treated, each unit containing a predetermined quantity of a peptide embodied by the invention calculated to produce the desired therapeutic or prophylactic effect in association with the carrier used.

When the dosage unit form is a capsule, it may contain in addition to one or more of the above ingredients a liquid carrier. Various other ingredients may be present as coatings or to otherwise modify the physical form of the dosage unit. For instance, tablets, pills or capsules may be coated with shellac, sugars or both.

In addition, a pharmaceutical composition may contain a vector of the invention capable of transfecting target cells. The vector may for instance, be packaged into a suitable virus for delivery of the vector into target cells as described above.

Pharmaceutical compositions will generally contain at least about 1% by weight of the peptide or dendrimer. The percentage may of course be varied and may conveniently be between about 5% w/w to about 80% w/w of the composition or preparation. As will be appreciated, the amount of the peptide in such compositions will be such that a suitable effective dosage will be delivered to the subject taking into account the proposed mode of administration. Preferred oral compositions according to the invention will contain between about 0.1 µg and 4000 mg of the peptide.

Typically, the peptide will be administered at a dosage of the peptide of up to about 200 mg/kg body weight of the individual when administered orally, and preferably in a range of from about 20 mg/kg to 40 mg/kg body weight. In at least some embodiments, the peptide will be administered to provide an oral dosage of the peptide in a range of from about 5 to 25 mg/kg body weight, usually in a range of from about 5 mg/kg to about 20 mg/kg and more usually, in a range of from 10 mg/kg to about 20 mg/kg. When administered as a peptide dendrimer, up to about 20 g of the dendrimer may be administered per day (e.g., 4 oral doses each comprising 5 g of the dendrimer).

The dosage of the peptide will depend on a number of factors including whether the peptide is to be administered for prophylaxis or treatment, the condition for which the agent is intended to be administered, the severity of the condition, the age of the subject, and related factors including weight and general health of the subject as may be determined by the physician or medical attendant in accordance with accepted principles. For instance, a low dosage may initially be given which is subsequently increased at each administration following evaluation of the subject's response. Similarly, frequency of administration may be determined in the same way that is, by continuously monitoring the subject's response between each dosage and if necessary, increasing the frequency of administration or alternatively, reducing the frequency of administration.

The route of administration of a pharmaceutical composition will again depend on the nature of the cancer for which the composition is to be administered. Suitable routes of administration include but are not limited to orally, intravenously, subcutaneously, rectally, and topically. With respect to intravenous routes, particularly suitable routes are via injection into blood vessels which supply a tumour or particular organs to be treated. The peptides can also be delivered into cavities such for example the pleural or peritoneal cavity, or be injected directly into tumour tissue.

Indeed, in one or more embodiments, the peptide is delivered to the mammal by ingestion or consumption of the peptide or of a bacterium or other organism such as yeast expressing the peptide or expressing a protein that upon pepsin digestion releases a peptide embodied by the invention. This can, for example be achieved by consuming a cheese containing a *Brevibacterium* or other bacterium that produces the peptide or protein the pepsin cleavage of which releases a peptide embodied by the invention or which otherwise effects a prophylactic or therapeutic treatment embodied by the invention. Delivery of the peptide agent can also be achieved by directly administering the bacterial organism expressing the peptide or protein to the mammal.

The *Brevibacterium* (e.g., *B. linens*) or other organism can be administered in capsule or tablet form, or in loose powder form. Alternatively, the *B. linens* or other organism can be administered via the consumption by the mammal in the form of a foodstuff or nutritive supplement suitable for mammalian consumption. This also applies to purified forms of the peptide or protein. Any suitable foodstuff or supplement known to those skilled in the art can be utilized as the carrier. For example, the bacterium, peptide or protein can be administered by consumption of a cheese, or a fermented or non-fermented beverage such as a dairy-based beverage (fermented or non-fermented), or fruit juice.

Moreover, the *B. linens* or other organism can be administered in live or killed form. Killing of the organism can be achieved by sonication or any other suitable method known to those skilled in the art for the purpose of the invention. The dosage of *B. linens* or other organism can be in a range of from $10^8$ to $10^{12}$ organisms administered in a single dose or in multiple doses. It will be understood that dosages of about $10^9$, $10^{10}$ or $10^{11}$ are also expressly encompassed. An extract of the organism can for example be a sonicate fraction or other fraction of a lysed or disrupted preparation of the organism. For example, when the organism is a suitable bacterium, it can be administered in live form or as a bacterial cellular preparation in a suitable carrier. In some embodiments, a lysed or sonicated and/or fractionated extract of the bacterial preparation may be provided in a suitable carrier for use as a pharmaceutical composition or as a nutritive supplement While the use of bacterial organisms to produce the proteins and peptides of the invention is described, other organisms may also be used to express/produce the proteins or peptides of the invention. For example, the proteins or peptides can be expressed in yeast to provide a cellular preparation or an extract thereof via sonication, lysis and/or fractionation prior to administration to a subject or inclusion in a nutritive supplement.

Suitable pharmaceutically acceptable carriers and formulations useful in compositions of the present invention may for instance be found in handbooks and texts well known to the skilled addressee, such as "Remington: The Science and Practice of Pharmacy (Mack Publishing Co., 1995)", the contents of which is incorporated herein in its entirety by reference.

The cancer treated by a peptide in accordance with an embodiment of the invention can be selected from the group consisting of carcinomas, sarcomas, lymphomas, head and neck cancers, leukaemias, and cancer of the liver, tongue, salivary glands, gums, floor and other areas of the mouth, oropharynx, nasopharynx, hypopharynx and other oral cavities, oesophagus, pancreas, gastrointestinal tract, stomach, small intestine, duodenum, colon, colorectum, rectum, gallbladder, pancreas, larynx, trachea, bronchus, lung including non-small cell lung carcinoma, breast, uterus, cervix, ovary, vagina, vulva, prostate, testes, penis, bladder, kidney, thyroid, bone, bone marrow, and skin including melanoma. Typically, the cancer will be of epithelial origin. Most usually, the cancer will be selected from the group consisting of cancers of the gastrointestinal tract, including stomach cancer, colon cancer and colorectal cancer.

A peptide or dendrimer as described herein can be co-administered with one or more other compounds or drugs conventionally used for the treatment of cancer. For example, the peptide or dendrimer may be co-administered in combination or in conjunction with one or more chemotherapeutic drugs selected from the group consisting of conventional metal and non-metal based anticancer drugs, and other anti-cancer drugs. The metal based drugs can be organic, inorganic, mixed ligand co-ordination compounds or chelates, including complexes of platinum and palladium. Examples of platinum based chemotherapeutic drugs include cisplatin (cis-diamminedichloroplatinum(II), oxaliplatin ([Pt((1R), (2R)-cyclohexane-1,2-diamine)(oxalato)] complex, and carboplatin (cis-diammine(cyclobutane-1,1-dicarboxylato) platinum(II). Examples of non-metal chemotherapeutic drugs include paclitaxel, gleevac, docetaxel, taxol, 5-fluorouracil, doxorubicin, cyclophosphamide, vincristine (Oncovin), vinblastine, vindesin, camplothecin, gemcitabine, adriamycin, and topoisomerase inhibitors such as irinotecan (CPT-11). Other anticancer drugs that may be co-administered with the peptide/dendrimer include src kinase inhibitors, and anti-cancer polypeptides such as those having anti-src kinase activity or incorporating a binding domain of a β integrin subunit (or a modified form thereof) in non-dendrimeric form.

The present invention is further exemplified below with reference to a number of non-limiting Examples.

Example 1

Figure 3:
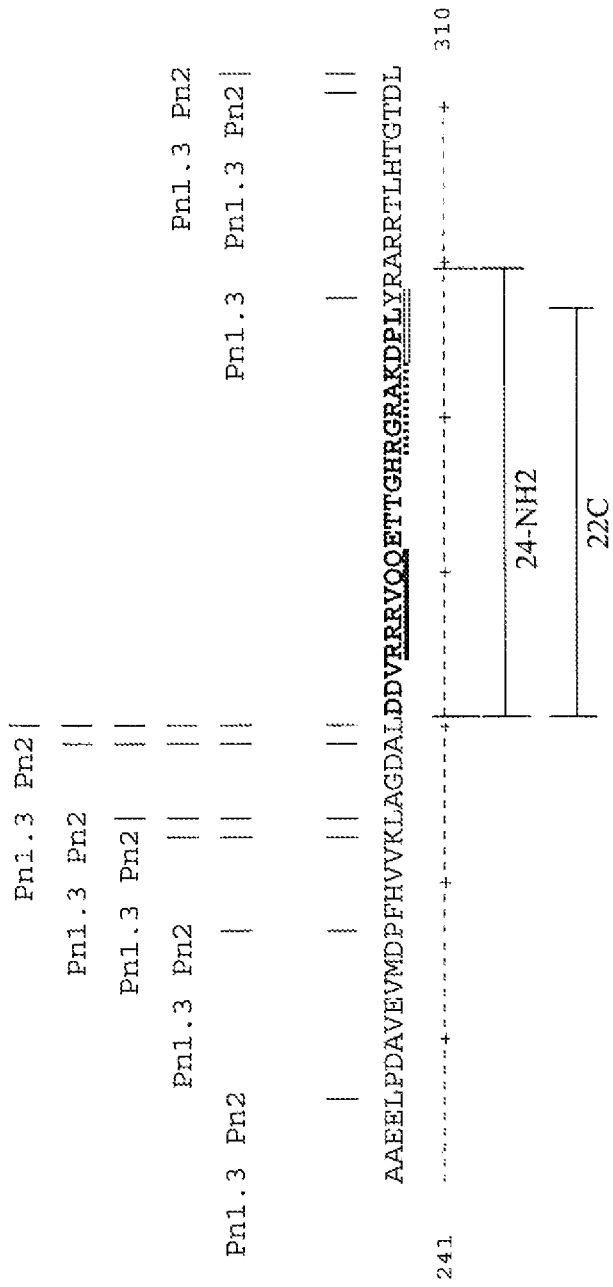
FIG. 3 shows a partial amino acid sequence (SEQ ID No. 8) of the putative DNA transposase (GenBank Accession No. O68604) of *B. linens* from which the peptide (SEQ ID No. 4)

Theoretical Pepsin Digestion of a *Brevibacterium linens* Putative DNA Transposase Theoretical pepsin digestion (Expasy Peptide Cutter) of a putative DNA transposase (Accession No. O68604) derived from the bacterium *Brevibacterium linens* revealed a peptide, hereinafter referred to as 22C (SEQ ID No. 4) (FIG. 3), containing a number of motifs that resembled functionally defined linear peptide sequences. The 22C peptide contains a linear cationic sequence RGRAK (SEQ ID No. 1) (FIG. 3; dotted underlining) which is a feature of a class of cationic antimicrobial peptides (Jin et al., 2005); a partial NPXY motif (SEQ ID. 2), specifically DPL (SEQ ID No. 16) (FIG. 3; double underlining) at the carboxyl terminus which is a known docking site for intracellular adaptor and scaffolding proteins and may play a role in the regulation of signal transduction pathways (Trommsdorff et al. 1998), and a basic peptide sequence RRRVQQ (SEQ ID No. 5) (FIG. 3; solid underlining) which resembles a portion of the TAT 48-60 peptide GRKKRRQRRRPPQ (SEQ ID No. 3), the similar segment being underlined. The TAT 48-60 peptide is one of a number of peptides that have demonstrated ability to transport small or large molecules across cell membranes.

A BLAST-P analysis using an extended version of peptide 22C, hereinafter referred to as peptide 24-NH2 (SEQ ID. No. 7) (FIG. 3), that included the entire NPLYR (SEQ ID. 23) homologous motif was carried out using www.Ncbi.nlm.nih.gov/BLAST/ set at default parameters. This search produced six 24-NH2-like sequences (SEQ ID No. 9-14) all resident in putative transposase proteins (FIG. 4). Conserved amino acids between the six sequences occurred in the TAT-like motif, in the linear cationic sequence found in cationic antimicrobial peptides, and in the partial NPXY motif (SEQ ID No. 2) (FIG. 4; residues in bold). The sequences differed, however, in the profile of peptides produced following theoretical pepsin digestion (Expasy Peptide Cutter program) (FIG. 4; digestion fragments underlined), with pepsin digestion generally compromising the integrity of the three defining motifs identified in 22C (SEQ ID No. 4). It is the combination of these motifs within 22C that suggest the peptide can cross the cell membrane and effect intercellular signaling pathways involved in cell growth.

Example 2

Assessment of the Antiproliferative Activity of Peptides 24-NH2 (SEQ ID No. 7), 22C (SEQ ID No. 4) and Modified Forms of Peptide 22C (SEQ ID No. 4)

2.1 Culture of HT29 Human Colorectal Adenocarcinoma Cells, SW480 Colon Carcinoma Cells and MKN45 Gastric Carcinoma Cells HT29 (colorectal adenocarcinoma) (ATCC HTB-38; Manassas, Va.). SW480 colon carcinoma cells (ATCC) and MKN45 gastric carcinoma cells (Cancer Research Laboratory, University of New South Wales, Sydney, Australia) were maintained in DMEM (Invitrogen, Carlsbad, Calif.) containing 10% heat inactivated, filtered, fetal bovine serum (FBS; Invitrogen) and 20 mM HEPES buffer. Cell culture was carried out in an incubator set at 37° C. in 5% $CO_2$ in air. Cells were grown to approximately 80% confluence in tissue culture flasks before being recovered from the substrate by trypsinisation. Briefly, resident culture media was removed and cells washed twice with sterile phosphate-buffered saline solution. A volume of 10× trypsin in EDTA (to provide 0.5% trypsin w/w) was added in sufficient quantity to cover the cells. When cells had sufficiently detached from the substrate, trypsin activity was stopped by the addition of 10% FBS in DMEM. Detached cells were transferred to a conical sterile tube and the suspended cells passaged ten times up and down through a 10 ml pipette to produce a single cell suspension suitable for counting. The number of viable cells was determined using a viability stain (Trypan blue) and counting using a haemocytometer.

2.2 MTT Cell Proliferation Assay

The MTT cell proliferation assay measures cell proliferation rate and, in instances where cell viability is compromised, the assay indicates a comparative reduction in cell viability.

Single cell suspensions of viable trypsinised cells were seeded into 96-well tissue culture plates at a density of $2 \times 10^3$ cells per well in a volume of 100 ul of culture media with or without serum. A set of triplicate wells was prepared for each concentration of compound being tested. Additional sample wells containing untreated cells or media alone were set up in each treatment plate and processed in parallel as reference controls. A zero-time plate of untreated cells and media-alone wells was simultaneously prepared and MTT assay carried out on this plate at the time of compound addition to treatment plates (see procedure below). All plates were cultured for 24 hours before addition of compound.

Appropriate concentrations of compound were prepared by dilution of freshly prepared sterile 1 mM stock solutions in normal saline into cell culture media to give a final culture-well volume of 200 ul. The zero-plate was processed by addition of MTT (3-(4,5-dimethylthiazolyl-2)-2,5-diphenyltetrazolium bromide; Sigma, St Louis Mo.) at this time. Cell culture was continued for a further 48 hours before addition of 20 ul of MTT in PBS (5 mg/ml, 0.2 um filter sterilised). After a 3 hour incubation in the presence of MTT plates were spun at 450 g for 5 minutes, supernatant removed by gentle suction and precipitated tetrazolium salt resuspended into 150 µl DMSO:glycine (0.1M glycine, 0.1M NaCl pH 10.5) (6:1 v/v) solution. Plates were gently vortexed to complete solubilisation of crystalline material and absorbance read at 540 nm using a microplate reader. Sample data were processed to determine the comparative growth of treated samples relative to untreated controls. All experiments were performed on at least three occasions.

2.3 Results

The antiproliferative activity of the peptides of interest was measured in MTT cell proliferation assays as described above. Peptide 24-NH2 (SEQ ID No. 7) was synthesized and amidated to provide protection from the potential of degradation by serum-derived exopeptidases contained in serum-supplemented cell culture medium. Many naturally occurring mammalian peptides are modified in this manner as a means of prolonging serum or plasma half-life (Adessi and Soto, 2002).

In particular, HT29 human colorectal adenocarcinoma cells were challenged with peptide 24-NH2 (SEQ ID No. 7) via MTT assay (72 hours) and the results are shown in FIG. 5a. As can be seen, the results indicate that peptide 24-NH2 depresses the in vitro cell proliferation of colon cancer cells by up to 36% at a concentration of 50 µM.

Figures 5B, 5C:
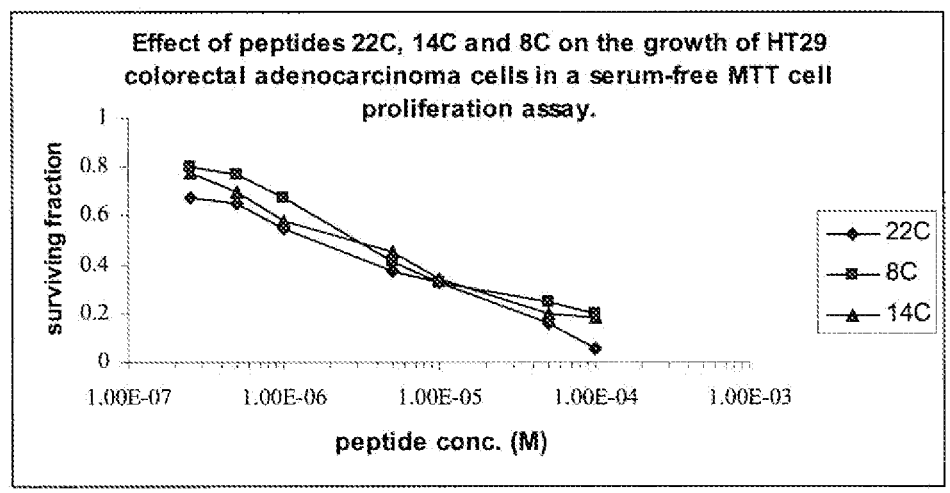

Antiproliferative activity of peptide 22C (SEQ ID No. 4) was then tested via MTT assay but under serum-free culture conditions. A free —COOH group was included at the carboxyl-terminus of peptide 22C to mimic the peptide format which would be produced following gastric pepsin digestion of the bacterial transposase protein. Two peptide derivatives from 22C, one referred to as 14C(H-DDVRRRVQQETTGH-COOH) (SEQ ID NO.) (FIG. 5b) containing the TAT-like motif, and the other referred to as 8C (FIG. 5b; SEQ ID No. 17) containing the linear cationic sequence and partial NPXY-motif (SEQ ID No. 2) were tested in parallel (FIG. 5c). All peptides inhibited the growth of HT29 colon cancer cells in the absence of serum (72 hour assay).

Figure 5D:
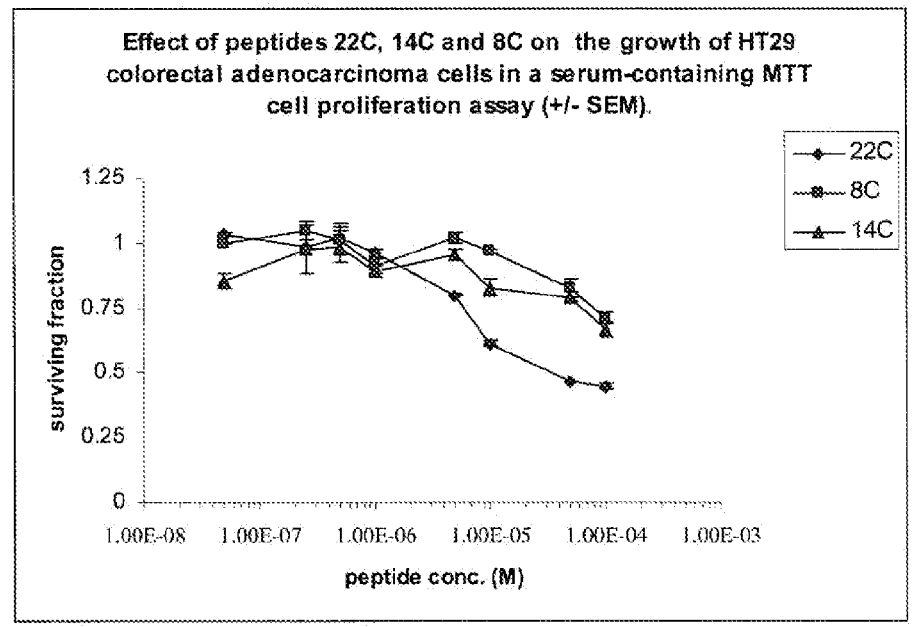

The same peptides were then tested via MTT assay containing serum (24 hour assay) (FIG. 5d). The results indicate that peptide 22C depresses the in vitro cell proliferation of colon cancer cells by up to 54% at a concentration of 35 uM and is more effective than peptide 14C and peptide 8C in serum-supplemented culture media (FIG. 5d) and moreover, is more effective than the 24-NH2 peptide (FIG. 5a).

The growth inhibitory effect of peptide 22C on HT20 colorectal adenocarcinoma cells in the presence of serum was subsequently compared with its effect on SW480 human colon carcinoma cells and MKN45 human gastric carcinoma cells via a 48 hour MTT assay. The 22C peptide was found to inhibit proliferation of SW480 and MKN45 cells to a similar degree as for HT29 cells in the 48 hour assay (FIG. 6).

It will be appreciated by persons skilled in the art that numerous variations and/or modifications may be made without departing from the scope of the invention as broadly described. The present embodiments are, therefore, to be considered in all respects as illustrative and not restrictive.

LITERATURE REFERENCES

Adessi C and Soto C. Converting a peptide into a drug: strategies to improve stability and bioavailability. *Curr Med. Chem.* 2002; 9:963-978.

Cloninger, M J, Biological applications of dendrimers. *Curr. Opin. Chem. Biology.* 6, 742-748 (2002).

De Boer P A, Crossley, R E, and Rothfield, L I. A division inhibitor and topological specific factor coded for by the miicell locus determine proper placement of the division septum in *E. coli. Cell* 1989, 56; 641-649.

Derossi D, Calvet S, Trembleau A et al *J Biol Chem* 1996, 271: 18188-18193.

Derossi D, Joliot A H, Chassaing G and Prochiantz A. *J Biol Chem* 1994, 269: 10444-10450.

Jin Y, Hammer J, Pate M, Zhang Y, Zhu F, Zmuda E and Blazyk J. Antimicrobial Activities and Structures of Two Linear Cationic Peptide Families with Various Amphipathic-Sheet and -Helical Potentials. *Antimicrobial Agents and Chemotherapy* 2005; 49: 4957-4964.

Lee, C C, MacKay, J A, Frechet, J M. and Szoka, F C. Designing dendrimers for biological applications. Nature Biotech. 23, 1517-1526 (2005). MacDiamid, J A., Mugridge, N B., Wiess, J C. Bacterially derived 400 nm particles for encapsulation and cancer cell targeting of chemotherapeutics. Cancer Cell 2007; 11; 431-445.

Needlemen, S. B., and Wunsch, C. C. A general method applicable to the search for similarities in the amino acid sequence of two proteins. *J. Mol. Biol.* 48(3), 443-53, 1970.

Onraedt A, Soetaert W and Vandamme E. Industrial importance of the genus *Brevibacterium*. *Biotechnology Letters.* 2005; 27:527-533.

Pooga M, Hallbrink, Zorko M, Lange I U. *Faseb J* 1998, 12(1), 67-77

Prochiantz A, *Curr Opin Neurobiol* 1996, 6(5): 629-634.

Rice P A and Baker T A Comparative architecture of transposase and integrase complexes. 2001 *Nature Structural Biology* 8:302-307.

Sadler, K. and Tam, J P. Peptide dendrimers: applications and synthesis. *Rev. Mol. Biotechnology.* 90, 195-229, (2002).

Trommsdorff M, Borg J-P, Margolis B, and Herz J. Interaction of Cytosolic Adaptor Proteins with Neuronal Apolipoprotein E Receptors and the Amyloid Precursor Protein. *J Biol. Chem.* 1998; 273: 33556-33560.

The invention claimed is:

1. A purified, anti-cancer, 20 to 30 amino acid length peptide comprising the amino acid sequence of SEQ ID NO:4.

2. The purified, anti-cancer peptide of claim 1, wherein said peptide consists of the amino acid sequence of SEQ ID NO:4.

3. The purified, anti-cancer peptide of claim 1, wherein said peptide is 22 to 24 amino acids in length and comprises the amino acid sequence of SEQ ID NO:4.

4. The purified, anti-cancer peptide of claim 1, wherein said peptide is 22 amino acids in length and comprises the amino acid sequence of SEQ ID NO:4.

5. The purified, anti-cancer peptide of claim 1 coupled to a facilitator moiety provided to facilitate passage of the peptide into a cancer cell.

6. A method for prophylaxis or treatment of cancer in a mammal, the method comprising the step of administering to the mammal an effective amount of the purified, anti-cancer peptide of claim 1.

7. The method of claim 6, wherein said peptide consists of the amino acid sequence of SEQ ID NO:4.

8. The method of claim 6, wherein said peptide is 22 to 24 amino acids in length and comprises the amino acid sequence of SEQ ID NO:4.

9. The method of claim 6, wherein said peptide is 22 amino acids in length and comprises the amino acid sequence of SEQ ID NO:4.

10. The method of claim 6, wherein said peptide is coupled to a facilitator moiety provided to facilitate passage of the peptide into a cancer cell.

11. A dosage unit form for the prophylaxis or treatment of cancer comprising the purified, anti-cancer peptide of claim 1.

12. The dosage unit form of claim 11, wherein said peptide consists of the amino acid sequence of SEQ ID NO:4.

13. The dosage unit form of claim 11, wherein said peptide is 22 to 24 amino acids in length and comprises the amino acid sequence of SEQ ID NO:4.

14. The dosage unit form of claim 11, wherein said peptide is 22 amino acids in length and comprises the amino acid sequence of SEQ ID NO:4.

15. The dosage unit form of claim 11, wherein said peptide is coupled to a facilitator moiety provided to facilitate passage of the peptide into a cancer cell.

16. The dosage unit form of claim 11, wherein the dosage unit form is selected from the group consisting of tablets, pills and capsules containing the peptide.

* * * * *

SEQUENCE LISTING

<160> NUMBER OF SEQ ID NOS: 22

<210> SEQ ID NO 1
<211> LENGTH: 5
<212> TYPE: PRT
<213> ORGANISM: Unknown
<220> FEATURE:
<223> OTHER INFORMATION: Description of sequence: consensus sequence

<400> SEQUENCE: 1

```
Arg Gly Arg Ala Lys
1               5

<210> SEQ ID NO 2
<211> LENGTH: 4
<212> TYPE: PRT
<213> ORGANISM: Unknown
<220> FEATURE:
<223> OTHER INFORMATION: Description of sequence: consensus sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Asn Pro Xaa Tyr
1

<210> SEQ ID NO 3
<211> LENGTH: 13
<212> TYPE: PRT
<213> ORGANISM: HIV-1

<400> SEQUENCE: 3

Gly Arg Lys Lys Arg Arg Gln Arg Arg Arg Pro Pro Gln
1               5                   10

<210> SEQ ID NO 4
<211> LENGTH: 22
<212> TYPE: PRT
<213> ORGANISM: Brevibacterium linens

<400> SEQUENCE: 4

Asp Asp Val Arg Arg Arg Val Gln Gln Glu Thr Thr Gly His Arg Gly
1               5                   10                  15

Arg Ala Lys Asp Pro Leu
            20

<210> SEQ ID NO 5
<211> LENGTH: 6
<212> TYPE: PRT
<213> ORGANISM: Brevibacterium linens

<400> SEQUENCE: 5

Arg Arg Arg Val Gln Gln
1               5

<210> SEQ ID NO 6
<211> LENGTH: 3
<212> TYPE: PRT
<213> ORGANISM: Brevibacterium linens

<400> SEQUENCE: 6

Asp Pro Leu
1

<210> SEQ ID NO 7
<211> LENGTH: 24
<212> TYPE: PRT
<213> ORGANISM: Brevibacterium linens

<400> SEQUENCE: 7

Asp Asp Val Arg Arg Arg Val Gln Gln Glu Thr Thr Gly His Arg Gly
1               5                   10                  15

Arg Ala Lys Asp Pro Leu Tyr Arg
            20
```

<210> SEQ ID NO 8
<211> LENGTH: 60
<212> TYPE: PRT
<213> ORGANISM: Brevibacterium linens

<400> SEQUENCE: 8

Ala Ala Glu Glu Leu Pro Asp Ala Val Glu Val Met Asp Pro Phe His
1               5                   10                  15

Val Val Lys Leu Ala Gly Asp Ala Leu Asp Asp Val Arg Arg Arg Val
            20                  25                  30

Gln Gln Glu Thr Thr Gly His Arg Gly Arg Ala Lys Asp Pro Leu Tyr
        35                  40                  45

Arg Ala Arg Arg Thr Leu His Thr Gly Thr Asp Leu
    50                  55                  60

<210> SEQ ID NO 9
<211> LENGTH: 24
<212> TYPE: PRT
<213> ORGANISM: Brevibacterium linens

<400> SEQUENCE: 9

Asp Val Cys Arg Arg Arg Val Gln Gln Ala Thr Cys Gly His Arg Gly
1               5                   10                  15

Arg Ala Gly Asp Pro Leu Tyr Lys
            20

<210> SEQ ID NO 10
<211> LENGTH: 24
<212> TYPE: PRT
<213> ORGANISM: Brevibacterium linens

<400> SEQUENCE: 10

Asp Glu Cys Arg Arg Arg Val Gln Leu Ala Thr Cys Gly His Arg Gly
1               5                   10                  15

Arg Ser Thr Asp Pro Leu Tyr Arg
            20

<210> SEQ ID NO 11
<211> LENGTH: 24
<212> TYPE: PRT
<213> ORGANISM: Brevibacterium linens

<400> SEQUENCE: 11

Asp Glu Cys Arg Arg Arg Val Gln His Asp Ile Leu Gly Arg Arg Gly
1               5                   10                  15

Arg Lys Asn Asp Pro Leu Tyr Lys
            20

<210> SEQ ID NO 12
<211> LENGTH: 24
<212> TYPE: PRT
<213> ORGANISM: Brevibacterium linens

<400> SEQUENCE: 12

Asp Glu Ala Arg Arg Arg Val Gln Gln Ala Pro Ser Gly Asn Arg Gly
1               5                   10                  15

Arg Thr Ser Asp Pro Leu Tyr Gly
            20

<210> SEQ ID NO 13
<211> LENGTH: 24

```
<212> TYPE: PRT
<213> ORGANISM: Brevibacterium linens

<400> SEQUENCE: 13

Thr Val Cys Arg Gln Arg Ile Gln Gln Ala Thr Thr Gly His Arg Gly
1               5                   10                  15

Arg Gly Gly Asp Pro Leu Tyr Gly
            20

<210> SEQ ID NO 14
<211> LENGTH: 22
<212> TYPE: PRT
<213> ORGANISM: Brevibacterium linens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 14

Asp Xaa Xaa Arg Arg Val Gln Gln Xaa Thr Xaa Gly His Arg Gly
1               5                   10                  15

Arg Xaa Lys Asp Pro Leu
            20

<210> SEQ ID NO 15
<211> LENGTH: 14
<212> TYPE: PRT
<213> ORGANISM: Brevibacterium linens

<400> SEQUENCE: 15

Asp Asp Val Arg Arg Arg Val Gln Gln Glu Thr Thr Gly His
1               5                   10

<210> SEQ ID NO 16
<211> LENGTH: 8
<212> TYPE: PRT
<213> ORGANISM: Brevibacterium linens

<400> SEQUENCE: 16

Arg Gly Arg Ala Lys Asp Pro Leu
1               5

<210> SEQ ID NO 17
<211> LENGTH: 17
<212> TYPE: PRT
<213> ORGANISM: Brevibacterium linens

<400> SEQUENCE: 17

Asp Arg Arg Arg Val Gln Gln Thr Gly His Arg Gly Arg Lys Asp Pro
1               5                   10                  15

Leu

<210> SEQ ID NO 18
<211> LENGTH: 5
<212> TYPE: PRT
```

```
<213> ORGANISM: Brevibacterium linens

<400> SEQUENCE: 18

Arg Ser Arg Ala Lys
1               5

<210> SEQ ID NO 19
<211> LENGTH: 5
<212> TYPE: PRT
<213> ORGANISM: Brevibacterium linens

<400> SEQUENCE: 19

Arg Gly Arg Ser Lys
1               5

<210> SEQ ID NO 20
<211> LENGTH: 5
<212> TYPE: PRT
<213> ORGANISM: Brevibacterium linens

<400> SEQUENCE: 20

Arg Ser Arg Ser Lys
1               5

<210> SEQ ID NO 21
<211> LENGTH: 3
<212> TYPE: PRT
<213> ORGANISM: Brevibacterium linens

<400> SEQUENCE: 21

Asn Pro Leu
1

<210> SEQ ID NO 22
<211> LENGTH: 5
<212> TYPE: PRT
<213> ORGANISM: Brevibacterium linens

<400> SEQUENCE: 22

Asn Pro Leu Tyr Arg
1               5
```